United States Patent [19]

Lee

[11] Patent Number: 4,627,834
[45] Date of Patent: Dec. 9, 1986

[54] APPARATUS FOR PERFORMING SUCTION LIPECTOMY

[76] Inventor: Hans Lee, Suite 200, 415 Morris St., Charleston, W. Va. 25301

[21] Appl. No.: 651,720

[22] Filed: Sep. 18, 1984

Related U.S. Application Data

[63] Continuation-in-part of Ser. No. 607,714, May 7, 1984.

[51] Int. Cl.$^4$ ............................................. A61M 31/00
[52] U.S. Cl. ........................................ 604/49; 604/93; 604/117; 604/902; 33/143 C; 33/169 B
[58] Field of Search ................... 604/35, 49, 93, 902, 604/22, 48, 110, 112, 113, 33, 45, , 39, 115–119, 268, 275, 289–290; 128/758, 759; 33/143 C, 169 B; 30/133, 286; 433/91, 93, 94

[56] References Cited

U.S. PATENT DOCUMENTS

| | | |
|---|---|---|
| 390,177 | 9/1888 | Lee . |
| 504,352 | 9/1893 | Heysinger .............................. 30/286 |
| 1,698,331 | 1/1929 | Gunter .................................. 433/91 |
| 1,749,919 | 3/1930 | Mierley . |
| 2,198,666 | 4/1940 | Gruskin ............................. 604/117 |
| 2,338,800 | 1/1944 | Burke . |
| 2,545,115 | 3/1951 | Son ..................................... 604/117 |
| 2,705,949 | 4/1955 | Silverman .......................... 604/117 |
| 2,715,899 | 8/1955 | MacLean . |
| 2,876,539 | 3/1959 | Ford ..................................... 30/286 |
| 3,920,001 | 11/1975 | Edwards . |
| 4,235,234 | 11/1980 | Whitney et al. ..................... 604/117 |
| 4,318,414 | 3/1982 | Schuster et al. ..................... 128/759 |
| 4,536,180 | 8/1985 | Johnson .............................. 604/902 |

Primary Examiner—C. Fred Rosenbaum
Assistant Examiner—Mario Costantino
Attorney, Agent, or Firm—Lowe, Price, LeBlanc, Becker & Shur

[57] ABSTRACT

A cannula is provided with a guide bar in which adjacent and overlying a hole formed in the cannula tip through which suction is applied to surgically aspirate fatty tissue is a guide surface adopted to contact and slide against the skin of a patient while the cannula tip is manually directed by the surgeon through the fatty tissue in reciprocating strokes. The guide surface maintains the tip at a constant depth within the tissue so that, upon completion of suction lipectomy, the desired amount of fatty tissue is surgically aspirated while leaving an even thickness layer of tissue intact. The guide surface includes an elevated portion spaced a greater distance from the cannula than a forward end of the guide bar having the guide surface. The elevated portion is manually engagable to permit two handed reciprocating movement of the cannula by the surgeon and to allow the surgeon to contact the patient's skin beneath the elevated portion to assist the cannula in the surgical procedure.

5 Claims, 5 Drawing Figures

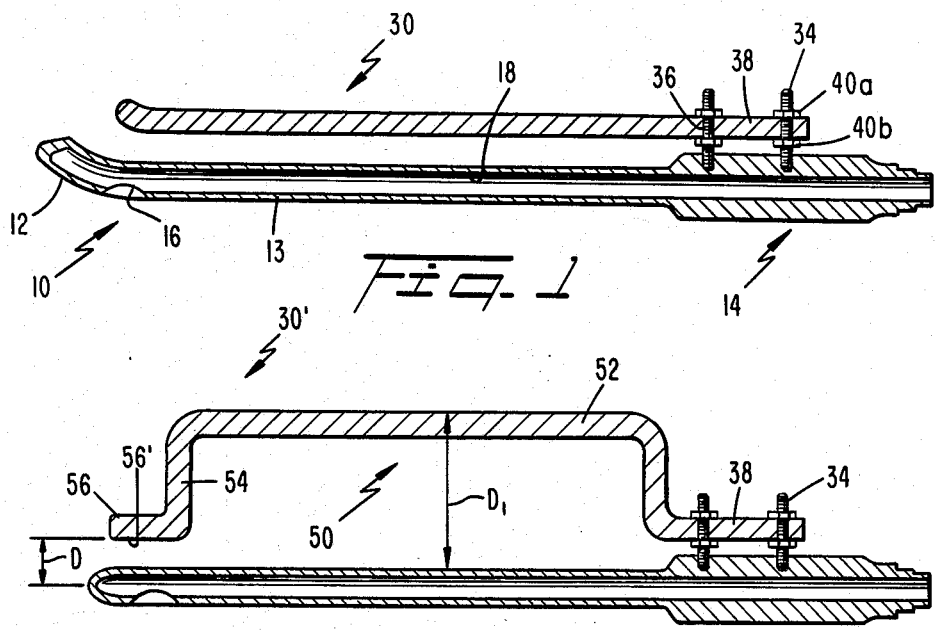
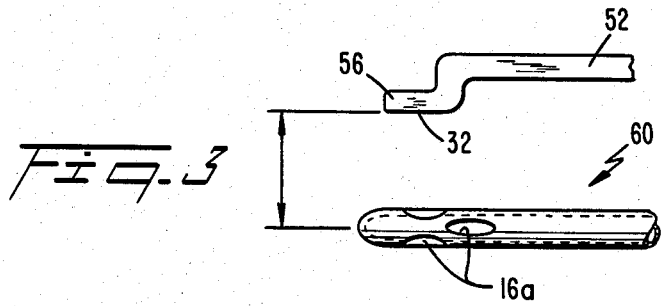
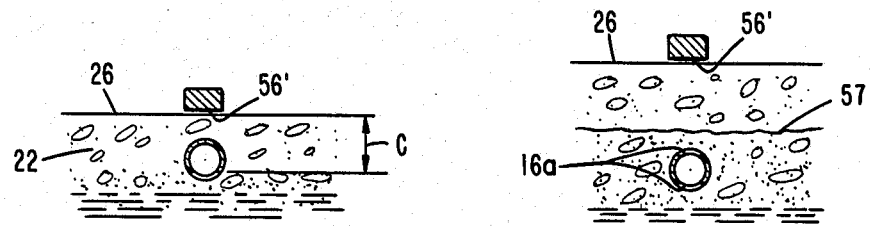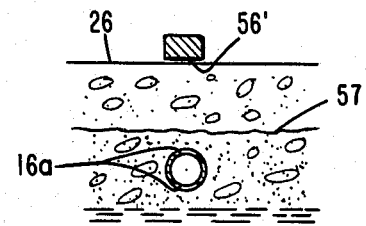

APPARATUS FOR PERFORMING SUCTION LIPECTOMY

RELATED APPLICATIONS

This application is a continuation in part of my copending U.S. patent application, Ser. No 607,714, filed May 7, 1984.

TECHNICAL FIELD

The present invention relates generally to surgical instruments and, more particularly, to a surgical cannula for use in performing suction lipectomy to remove excess accumulation of fatty tissue from a human body.

BACKGROUND ART

In my copending U.S. patent application, mentioned supra, there is disclosed an improved cannula provided with a guide bar extending in spaced, parallel relationship to the cannula body. One end of the guide bar is connected with bolts to the cannula. A forward free end of the guide bar, located adjacent and overlying one or more holes formed in the cannula tip through which suction is applied to surgically aspirate fatty tissue, is formed with a guide surface adapted to contact and slide against the patient's skin while the cannula tip is manually directed by the surgeon through the fatty tissue in reciprocating strokes. The guide surface maintains the tip at a constant depth within the tissue so that, upon completion of suction lipectomy, a desired amount of fatty tissue is surgically aspirated while leaving an even thickness layer of tissue intact.

The guide bar is capable of achieving the aforesaid results by allowing the surgeon to move the tip at constant depth through the tissue through a large number of repetative strokes necessary for adequate aspiration without rendering the surgical procedure fatiguing to the surgeon who is now able to grasp the gripping handle of the cannula with both hands.

While my improved cannula, discussed supra, is effective for guiding the cannula tip at constant depth within the tissue, surface portions of the guide bar formed adjacent the guide surface thereof (i.e., between the guide surface and handle) tend to contact the patient's skin together with the guide surface, increasing frictional contact between the skin and guide bar and requiring additional manual force and exertion by the surgeon to reciprocate the cannula. Also, since the guide bar is parallel to the cannula and spaced fairly close thereto, two handed operation is limited to positioning both hands on the gripping portion of the cannula formed at one end thereof opposite the tip. Thus, considerable force is still required to reciprocate the tip through the fatty tissue although the tip is desirably maintained by the guide surface at constant depth. Furthermore, it is often desirable for the surgeon to place his non dominant hand (e.g., left hand if the surgeon is right-handed) on the skin under the guide bar to provide counter pull or counter push against the cannula during reciprocating movement thereof during suction lipectomy. However, the close, parallel spacing of the guide bar tends to prevent the surgeon from contacting the skin, as aforesaid. Also, the close parallel spacing between the guide bar and cannula in my previous invention often renders the surgical procedure difficult when performing surgical lipolysis on areas of the body having sharp contours (e.g., the hips) since surfaces of the guide bar formed adjacent the guide surface tend to contact the skin. A similar problem occurs when attempting to remove deep fatty tissue of the abdominal wall below the Scarpa's fascia.

It is accordingly an object of the present invention to provide an improved cannula that is easily guided by the surgeon at a constant depth so that a desired amount of fatty tissue is surgically aspirated while leaving an even thickness layer of tissue intact.

Another object is to provide an improved cannula that facilitates manuveurability and controllability by permitting two-handed gripping of the cannula by the surgeon during surgical aspiration.

Yet a further object is to provide a cannula that is easy for the surgeon to manipulate, rendering lypolysis less fatiguing for the surgeon to improve safety.

Still another object is to provide an improved cannula that allows the surgeon to place his or her non-dominant hand on the skin under the guide bar for counter pull or counter pushing action against the cannula.

A further object is to provide a cannula that is capable of removing deep fatty tissue from the abdominal wall, such as fatty tissue located below the Scarpa's fascia, and other areas of the body having sharp contours.

DISCLOSURE OF THE INVENTION

An improved cannula for surgically aspirating subcutaneous fatty tissue, in accordance with the present invention, comprises a cannula having a tip and a handle at opposite ends thereof. The tip is formed with one or more holes, a longitudinal passage extends through the cannula in communication with the hole(s). The passage is connectable to a source of vacuum so that suction can be applied to surgically aspirate fatty tissue through the hole when the tip is implanted in tissue. A guide bar is attached to the cannula for maintaining the hole at a predetermined, desired depth within the tissue as the tip is manually directed by a surgeon. The guide bar is formed with an elevated portion between opposite ends thereof to be gripped with one hand of the surgeon while the surgeon's other hand engages the handle portion of the cannula to thereby facilitate surgical manipulation of the cannula.

The elevated portion of the guide bar preferably extends parallel to a major portion of the cannula and is spaced a predetermined distance $D_1$ therefrom. The forward end of the elevated portion is offset 90 degrees towards the cannula so that the free end of the guide bar is parallel to the cannula tip with the guide surface spaced a predetermined distance $D$ from the tip, wherein $D_1 > D$. In operation, only the guide surface is in sliding contact with the skin surface to control the depth at which the cannula tip reciprocates through the fatty tissue; the elevated portion of the guide bar is spaced from the skin surface to be gripped by the surgeon or to enable the surgeon to manually contact the skin beneath the elevated portion to assist in manipulation of the cannula.

Still other objects of the present invention will become readily apparent to those skilled in this art from the following description wherein there is shown and described a preferred embodiment of this invention simply by way of illustration of one of the best modes contemplated for carrying out the invention. As will be realized, the invention is capable of other different embodiments, and its several details are capable of modifications in various, obvious respects, without departing from the invention. Accordingly, the drawing and description will be regarded as illustrative in nature and not as restrictive.

BRIEF DESCRIPTION OF THE DRAWING

FIG. 1 is a side elevational view of my improved cannula as described in my copending U.S. patent application mentioned above;

FIG. 2 is a side elevational view of further improvements to the cannula in accordance with the present invention;

FIG. 3 is a view similar to FIG. 2 showing a further embodiment of the cannula according to the present invention; and FIGS. 4 and 5 are enlarged fragmentary views showing the tip of the improved cannula of the present invention inserted into fatty tissue through an incision prior to surgical aspiration.

BEST MODE FOR CARRYING OUT THE INVENTION

FIG. 1 is an illustration of a cannula 10 on which is mounted a guide bar 30 as shown and described in my previous copending U.S. patent application, mentioned supra. Cannula 10 has a tip 12 and a handle 14 formed at opposite ends of an elongate, straight tubular section 13. Tip 12 can be inclined upward from straight section 13 at an angle of about 30 degrees or can be formed as a straight portion (FIG. 2) or inclined downward (not shown) depending on what portion of the body suction lipectomy is to be performed. A suction hole 16 in communication with passage 18 is formed in the cannula wall in tip 12. As depicted in FIG. 3, plural suction holes 16a can also be provided in tip 12 for particular surgical applications as discussed more fully below.

Guide bar 30 has a guide surface 32 pressed by the surgeon into constant contact with skin 26 so that suction hole 16 remains at constant depth during reciprocation of the cannula. The guide bar 30 is an elongate member that extends in spaced, parallel relationship of cannula 10 and is connected to the cannula by means of a pair of threaded bolts 34 secured to handle 14. Bolts 34 respectively pass through longitudinally spaced holes 36 formed at one end 38 of bar 30 overlying the handle. The diameter of through holes 36 is larger than the external threaded diameter of bolts 34, enabling the guide bar to slide on the bolts to vary the spacing between the guide and cannula. Other types of attachment means is contemplated so long as the guide bar does not move (spread apart) relative to the cannula during the suction lipectomy procedure. Nuts 40a, 40b are threaded on to each bolt 34 to fix bar 30 a predetermined distance from the cannula.

Referring now to FIG. 2 wherein improvements to the cannula depicted in FIG. 1 are shown, guide bar 30' of the present invention comprises a U-shaped elevated portion 50 having a main straight section 52 spaced a distance D1 from the cannula body. The distance D1 is sufficient to allow the surgeon to grip section 52 with one hand without contacting the patient's skin or cannula body. The distance D1 is also sufficient to enable the surgeon to place his hand under the section 52 on the patient's skin to manually stretch the skin or provide manual counter force against the cannula during the suction lipectomy.

The forward end portion 54 of elevated portion 50 is offset 90 degrees from section 52 towards the cannula and terminates in distal end 56 having a lower guide surface 56' (similar to guide surface 32) that extends generally parallel to the cannula tip. In use, the guide surface 56' is positioned to rest upon skin 26 so that the cannula hole is embedded in tissue 22 at a predetermined desired depth C determined by the aforesaid nut and bolt arrangement. The cannula hole is maintained at constant depth by the surgeon during reciprocating movement of the cannula by virtue of guide surface 56' being easily pressed in sliding contact with the skin.

In my prior cannula depicted in FIG. 1, there exists a tendency for surface portions of guide bar 30 formed immediately adjacent to guide surface 32 to contact the skin surface during the surgical procedure tending to increase frictional contact with the skin. However, by elevating a major portion 52 from the cannula body as in the present invention, only guide surface 56' remains in contact with the skin surface to facilitate reciprocating movement of the cannula through the fatty tissue. Furthermore, by providing guiding contact only through guide surface 56', it becomes easier to maintain the guide surface in contact with the skin when performing the surgical procedure on various parts and thereby different contours of the body (i.e., flat, concave or convex) since surface portions that are otherwise formed immediately adjacent the guide surface in the guide bar 30 of my previous invention are now elevated away from the patient's skin.

The elevated portion 50 of my improved guide bar 30' of the present invention also facilitates removal of deep fatty tissue from the abdominal wall, such as the layer of fatty tissue located beneath the Scarpa's fascia 57 as depicted in FIG. 5. Preferably, removal of the fatty tissue from the abdominal wall, such as the layer of fatty tissue located beneath the Scarpa's fascia 57 is facilitated by use of the multi-holed cannula 60 depicted in conjunction with guide bar 30' of the present invention. The overlying guide surface 56' provides positive control over the depth at which the cannula tip reciprocates to prevent deeper penetration and thereby avoid damage to internal organs. However, in removing the layer of fatty tissue below the Scarpa's fascia, it is not necessary to maintain contact between guide surface 56' and the patient's skin since the Scarpa's fascia situated above the cannula tip prevents excessive removal of fat.

The foregoing description of the preferred embodiment of the invention has been presented for purposes of illustration and description. It is not intended ot be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A device for surgically aspirating subcutaneous fatty tissue and the like from an animate body, comprising:
   (a) a cannula having a tip and a handle at opposite ends thereof, the tip being formed with a hole and a longitudinal passage extending through the cannula in communication with the hole, said passage being connectable to a source of vacuum so that suction can be applied to surgically aspirate fatty tissue through the hole when the tip is inserted into the tissue;

(b) a guide bar having one end connected to the cannula at a portion thereof remote from the tip and an opposite end portion terminating adjacent the hole and spaced a first predetermined distance D from the tip, said opposite end having a guide surface in contact with, during surgery, a portion of the skin overlying the fatty tissue to limit the depth at which the hole penetrates the tissue, said guide bar including an elevated portion formed between the guide surface and the said one end of the guide bar and spaced a second predetermined distance D1 from a part of the cannula formed adjacent said elevated portion, wherein D1>D, said elevated portion being manually engageable by one hand of the surgeon while the surgeon's other hand engages the gripping portion of the cannula to thereby facilitate surgical manipulation of said device by allowing the surgeon to manually direct the length of the cannula and the tip through the tissue in reciprocating strokes with the guide surface being in substantially constant contact with the surface of said skin overlying the fatty tissue during said strokes; and (c) means for connecting the guide bar to the cannula.

2. The device of claim 1, wherein said guide bar is a U-shaped bar.

3. The device of claim 2, wherein said elevated portion includes a main straight section spaced distance D1 and extending generally parallel along a major length of the cannula, a front portion of the straight section being offset towards the cannula and including a forward projecting distal end formed with said guide surface.

4. A method of surgically aspirating to remove subcutaneous fatty tissue from desired areas of an animate body with a cannula having a tip and a handle at opposite ends thereof, the tip being formed with a hole, and a longitudinal passage extending through the cannula in communication with the hole, said passage being connected to a vacuum source so that suction is applied through the hole, said cannula further including a guide member having a guide surface spaced from the tip by a distance D and an elevated gripping portion spaced from the cannula by a distance D1, whereby D1>D, comprising the steps of:

(a) forming an incision to expose said subcutaneous fatty tissue;

(b) inserting the tip of the cannula through the incision so that the hole contacts the fatty tissue and the guide surface rests on the skin;

(c) applying suction through the hole while simultaneously moving the tip through the tissue in reciprocating strokes to surgically aspirate tissue in contact with the hole, said tip being moved through the tissue by manual grasping by the surgeon of said elevated portion of the guide member; and (d) guiding the hole within the tissue at a constant predetermined depth by maintaining the guide surface in constant contact with the skin while moving the tip through the tissue in said reciprocating strokes.

5. A device for surgically aspirating subcutaneous fatty tissue from an animate body using a cannula having a tip and handle formed at opposite ends thereof, the tip including a hole and a longitudinal passage extending through the cannula in communication with the hole, said passage being connectable to a source of vacuum so that suction can be applied to surgically aspirate fatty tissue through the hole when the tip is inserted into the tissue, comprising:

(a) a guide bar connected to the cannula, said guide bar having one end terminating adjacent the hole and spaced a first predetermined distance D from the tip, said one end having a guide surface in contact with, during surgery, a portion of the skin overlying the fatty tissue to limit the depth at which the hole penetrates the tissue, said guide bar further including an elevated portion formed between the guide surface and the opposite end of the guide bar and spaced at a second predetermined distance D1 from a part of the cannula formed adjacent said elevated portion, wherein D1>D, said elevated portion being manually engageable by one hand of the surgeon while the surgeon's other hand engages the gripping portion of the cannula to thereby facilitate surgical manipulation of said device by allowing the surgeon to manually direct the length of the cannula and the tip through the tissue in reciprocating strokes with the guide surface being in substantially constant contact with the surface of said skin overlying the fatty tissue during said strokes; and (b) means for connecting the guide bar to the cannula.

* * * * *